US009241944B2

(12) United States Patent
Farman et al.

(10) Patent No.: US 9,241,944 B2
(45) Date of Patent: Jan. 26, 2016

(54) METHODS AND COMPOSITIONS FOR STIMULATING REEPITHELIALISATION DURING WOUND HEALING

(75) Inventors: Nicolette Farman, Paris (FR); Francine Behar-Cohen, Paris (FR); Frédéric Jaisser, Paris (FR)

(73) Assignees: Institut National de la Santé et de la Recherche Médicale (INSERM), Paris (FR); Assistance Publique Hopitaux de Paris, Paris (FR); Universite Paris Descartes, Paris (FR)

( * ) Notice: Subject to any disclaimer, the term of this patent is extended or adjusted under 35 U.S.C. 154(b) by 0 days.

(21) Appl. No.: 13/703,923

(22) PCT Filed: Jun. 16, 2011

(86) PCT No.: PCT/EP2011/060039
§ 371 (c)(1),
(2), (4) Date: Feb. 19, 2013

(87) PCT Pub. No.: WO2011/157798
PCT Pub. Date: Dec. 22, 2011

(65) Prior Publication Data
US 2013/0143850 A1 Jun. 6, 2013

Related U.S. Application Data

(60) Provisional application No. 61/359,078, filed on Jun. 28, 2010.

(30) Foreign Application Priority Data

Jun. 16, 2012 (EP) .................................. 10305648

(51) Int. Cl.
*A61K 31/585* (2006.01)
*A61K 31/56* (2006.01)
*A61K 31/44* (2006.01)
*A61K 31/575* (2006.01)
*A61K 9/00* (2006.01)
*A61K 9/70* (2006.01)
*A61K 31/00* (2006.01)

(52) U.S. Cl.
CPC .............. *A61K 31/575* (2013.01); *A61K 9/0014* (2013.01); *A61K 9/0048* (2013.01); *A61K 9/7023* (2013.01); *A61K 31/00* (2013.01); *A61K 31/585* (2013.01)

(58) Field of Classification Search
USPC ......................................... 514/175, 178, 291
See application file for complete search history.

(56) References Cited

U.S. PATENT DOCUMENTS

| 7,015,210 B2 * | 3/2006 | Aiken ............................ 514/171 |
| 2001/0019721 A1 * | 9/2001 | Brandt et al. .................. 424/443 |
| 2002/0045746 A1 * | 4/2002 | Barton et al. ....................... 540/2 |
| 2004/0043026 A1 * | 3/2004 | Tuan et al. .................. 424/146.1 |
| 2004/0067916 A1 * | 4/2004 | Delyani et al. ................. 514/169 |
| 2007/0208134 A1 * | 9/2007 | Hunter et al. ................. 525/54.1 |
| 2009/0203628 A1 | 8/2009 | Marini |
| 2010/0068301 A1 * | 3/2010 | Hutchinson et al. .......... 424/646 |

FOREIGN PATENT DOCUMENTS

| EP | 0028 525 | * | 3/1980 |
| EP | 0410348 | * | 7/1990 |
| EP | 0582458 | * | 3/1993 |
| EP | 0 603 405 A1 | | 6/1994 |
| WO | 00/72883 A2 | | 12/2000 |
| WO | WO 00/72883 | * | 12/2000 |
| WO | 01/34132 A2 | | 5/2001 |
| WO | 2005/097196 A2 | | 10/2005 |
| WO | WO2006/002022 | * | 1/2006 |
| WO | 2008/078071 A1 | | 7/2008 |
| WO | 2010/038234 A1 | | 4/2010 |

OTHER PUBLICATIONS

Saching.com (2009).*
Mitts et al, (J. Investigative Dermatology (2010) 130, 2396-2406).*
Chernoff et al., "Epidermal growth factor and the onset of epithelial epidermal wound healing", Tissue and Cell, Jan. 1, 1990, pp. 123-135, vol. 22, No. 2, Churchill Livingstone Medical Journals, Edinburg, GB.
Silvana et al., "Cell Migration in BeWo Cells and the Role of Epithelial Sodium Channels", Journal of Membrane Biology, Nov. 13, 2009, pp. 1-13, vol. 232, No. 1-3, Springer-Verlag, NE.
Farman et al., "The mineralocorticoid receptor as a novel player in skin biology: beyond the renal horizon?", Experimental Dermatology, Feb. 1, 2010, pp. 100-107, vol. 19, No. 2.

* cited by examiner

*Primary Examiner* — Shirley V Gembeh
(74) *Attorney, Agent, or Firm* — Whitham, Curtis, Christofferson & Cook, P.C.

(57) ABSTRACT

The present invention relates to methods and compositions for stimulating reepithelialization during wound healing. More particularly, the present invention relates to a mmeralocorticoid receptor antagonist or an inhibitor of mineralocorticoid receptor gene expression for use in a method for stimulating reepithelialization of the skin or of the cornea during wound healing.

16 Claims, No Drawings

METHODS AND COMPOSITIONS FOR STIMULATING REEPITHELIALISATION DURING WOUND HEALING

FIELD OF THE INVENTION

The present invention relates to methods and compositions for stimulating reepithelialisation during wound healing.

BACKGROUND OF THE INVENTION

The primary function of the skin and cornea is to serve as a protective barrier against the environment. Loss of the integrity of portions of the skin or cornea as a result of injury or illness may lead to major disability or even death. Every year in the United States more than 1.25 million people have burns and 6.5 million have chronic skin ulcers caused by pressure, venous stasis, and diabetes mellitus. Many corneal problems are also caused by a loss of corneal epithelial integrity as observed in various diseases such as corneal ulcer, corneal erosion, keratitis and dry eye. Topical administration of drugs and surgery situations can also lead to delay of epithelial wound healing.

Wound healing is a dynamic, interactive process involving soluble mediators, blood cells, extracellular matrix, and parenchymal cells. Wound healing has 3 phases that overlap in time: vascular phase and inflammation, new tissue formation including reepithelialization, and tissue remodelling. Wounds are currently treated by applying an emergency treatment to a wounded site and waiting for the wounds to spontaneously heal via the biological recovering power of their own. However a chronic incomplete reepithelialisation may be observed and may lead to opportunistic infection, irreversible scarring and eventually cornea or skin impairment. Accordingly, the existent agents for wound healing do not have sufficient actions for stimulating reepithelialization so they are problematic in that they cannot completely heal wounds in a short period of time

SUMMARY OF THE INVENTION

The present invention relates to a mineralocorticoid receptor antagonist or an inhibitor of mineralocorticoid receptor gene expression for use in a method for stimulating reepithelialisation of the skin or of the cornea during wound healing.

DETAILED DESCRIPTION OF THE INVENTION

The present invention relates to a mineralocorticoid receptor antagonist for use in a method for stimulating reepithelialisation of the skin or of the cornea during wound healing.

It is to be understood that the term "wound" as used herein includes surgical incisions as well as wounds caused by accidental trauma.

Typically, cutaneous wounds may result from diabetic foot ulcer, venous stasis ulcer, burns. The term also includes delayed wound healing observed during corticoid treatments, delayed wound healing observed in elderly (aging defect), stress, delayed wound healing observed in diabetic patients, epithelialization defects of surgical scars or following skin grafts, finger cracks occurring after cold exposure, nail pathologies associated with delayed healing, foot blisters occurring during prolonged walk or run.

Corneal wounds may result from observed various diseases such as corneal ulcer, corneal erosion or trauma, keratitis and dry eye. Wound may also result from topical administration of drugs and surgery situations, such as keratoplasty and during the time-course of recovery from corneal graft.

As used herein the term "reepithelialization" refers to the migration of keratinocytes over the injured dermis and to the proliferation/maturation of keratinocytes that progressively cover the wound and restore barrier function; the same notion can be extended to the repair of the corneal epithelium.

As used herein, the term "mineralocorticoid receptor" or "MR" has its general meaning in the art and refers to the nuclear receptor subfamily 3, group C, member 2, (NR3C2) that is a receptor with high affinity for mineralocorticoids. The mineralocorticoid receptor is also called aldosterone receptor. The MR antagonistic or agonistic activity of a compound may be determined using various methods as described in J, Souque A, Wurtz J M, Moras D, Rafestin-Oblin M E. Mol Endocrinol. 2000 August; 14(8):1210-21; Fagart J, Seguin C, Pinon G M, Rafestin-Oblin M E. Mol Pharmacol. 2005 May; 67(5):1714-22 or Hellal-Levy C, Fagart J, Souque A, Wurtz J M, Moras D, Rafestin-Oblin M E. Mol Endocrinol. 2000 August; 14(8):1210-21. Typically, the transfection of the human mineralocorticoid receptor in COS cells together with a luciferase-expressing reporter gene allows to measure its transactivation activity in the presence of a candidate compound.

In the context of the present invention, mineralocorticoid receptor antagonists are preferably selective for the mineralocorticoid receptor as compared with the related receptors such as androgen receptor, estrogen receptors, glucocorticoid receptor, progesterone receptor, thyroid hormone receptors, peroxisome proliferator-activated receptors, retinoic acid receptor, farnesoid x receptor, pregnane x receptor, liver X receptor, vitamin D receptor, retinoid x receptor and the constitutive androstane receptor. By "selective" it is meant that the affinity of the antagonist for the mineralocorticoid receptor is at least 10-fold, preferably 25-fold, more preferably 100-fold, still preferably 500-fold higher than the affinity for the related receptors.

In one embodiment, the mineralocorticoid receptor antagonist is a low molecular weight antagonist, e. g. a small organic molecule. The term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more preferably up to 2000 Da, and most preferably up to about 1000 Da.

Typically, the mineralocorticoid receptor antagonists according to the invention generally are spirolactone-type steroidal compounds. The term "spirolactone-type" is intended to characterize a structure comprising a lactone moiety attached to a steroid nucleus, typically at the steroid "D" ring, through a spiro bond configuration. A subclass of spirolactone-type mineralocorticoid receptor antagonist compounds consists of epoxy-steroidal mineralocorticoid receptor antagonist compounds such as eplerenone. Another subclass of spirolactone-type antagonist compounds consists of non-epoxy-steroidal mineralocorticoid receptor antagonist compounds such as spironolactone.

The epoxy-steroidal mineralocorticoid receptor antagonist compounds used in the method of the present invention generally have a steroidal nucleus substituted with an epoxy-type moiety. The term "epoxy-type" moiety is intended to embrace any moiety characterized in having an oxygen atom as a bridge between two carbon atoms.

The term "steroidal," as used in the phrase "epoxy-steroidal," denotes a nucleus provided by a cyclopenteno-phenanthrene moiety, having the conventional "A", "B", "C", and "D" rings. The epoxy-type moiety may be attached to the cyclopentenophenanthrene nucleus at any attachable or substitutable positions, that is, fused to one of the rings of the steroidal nucleus or the moiety may be substituted on a ring member of the ring system. The phrase "epoxy-steroidal" is intended to embrace a steroidal nucleus having one or a plurality of epoxy-type moieties attached thereto.

Epoxy-steroidal mineralocorticoid receptor antagonists suitable for use in the present methods include a family of compounds having an epoxy moiety fused to the "C" ring of the steroidal nucleus. Examples include 20-spiroxane compounds characterized by the presence of a 9α,11α-substituted epoxy moiety, such as:

Pregn-4-ene-7,21-dicarboxylic acid, 9,11-epoxy-17-hydroxy-3-oxo-, γ-lactone, methyl ester, (7α,11α,17β)

Pregn-4-ene-7,21-dicarboxylic acid, 9,11-epoxy-17-hydroxy-3-oxo-, dimethyl ester, (7α,11α,17β)

3' H-cyclopropa[6,7]pregna-4,6-diene-21-carboxylic acid, 9,11-epoxy-6,7-dihydro-17-hydroxy-3-oxo-, γ-lactone, (6β,7β,11α,17β)

Pregn-4-ene-7,21-dicarboxylic acid, 9,11-epoxy-17-hydroxy-3-oxo-, 7-(1-methylethyl) ester, monopotassium salt, (7α,11α,17β)

Pregn-4-ene-7,21-dicarboxylic acid, 9,11-epoxy-17-hydroxy-3-oxo-, 7-methylethyl) ester, monopotassium salt, (7α,11α,17β)

3' H-cyclopropa[6,7]pregna-1,4,6-triene-21-carboxylic acid, 9,11-epoxy-6,7-dihydro-17-hydroxy-3-oxo-, γ-lactone (6β,7β,11α)

3' H-cyclopropa[6,7]pregna-4,6-diene-21-carboxylic acid, 9,11-epoxy-6,7-dihydro-17-hydroxy-3-oxo-, methyl ester, (6β,7β,11α,17β)

3' H-cyclopropa[6,7]pregna-4,6-diene-21-carboxylic acid, 9,11-epoxy-6,7-dihydro-17-hydroxy-3-oxo-, monopotassium salt, (6β,7β,11α,17β)

3' H-cyclopropa[6,7]pregna-1,4,6-triene-21-carboxylic acid, 9,11-epoxy-6,7-dihydro-17-hydroxy-3-oxo-, γ-lactone (6β,7β,11α,17β)

Pregn-4-ene-7,21-dicarboxylic acid, 9,11-epoxy-17-hydroxy-3-oxo-, γ-lactone, ethyl ester, (7α,11α,17β)

Pregn-4-ene-7,21-dicarboxylic acid, 9,11-epoxy-17-hydroxy-3-oxo-, γ-lactone, 1-methylethyl ester (7α,11α, 17β)

A particular benefit of using epoxy-steroidal mineralocorticoid receptor antagonists, as exemplified by eplerenone, is the high selectivity of this group of mineralocorticoid receptor antagonists for the mineralocorticoid receptor. The superior selectivity of eplerenone results in a reduction in side effects that can be caused by mineralocorticoid receptor antagonists that exhibit non-selective binding to related receptors, such as androgen or progesterone receptors.

These epoxy steroids may be prepared by procedures described in Grob et al., U.S. Pat. No. 4,559,332. Additional processes for the preparation of 9,11-epoxy steroidal compounds and their salts are disclosed in Ng et al., WO97/21720 and Ng et al., WO98/25948.

Of particular interest is the compound eplerenone ((Pregn-4-ene-7,21-dicarboxylic acid, 9,11-epoxy-17-hydroxy-3-oxo-, γ-lactone, methyl ester, (7α,11α,17β)) (CAS No. 107724-20-9), also known as epoxymexrenone. Eplerenone is a mineralocorticoid receptor antagonist and has a higher selectivity for mineralocorticoid receptors than does, for example, spironolactone. Selection of eplerenone as the mineralocorticoid receptor antagonist in the present method would be beneficial to reduce certain side-effects such as gynecomastia that occur with use of mineralocorticoid receptor antagonists having less specificity.

Non-epoxy-steroidal mineralocorticoid receptor antagonists suitable for use in the present methods include a family of spirolactone-type compounds defined by Formula I:

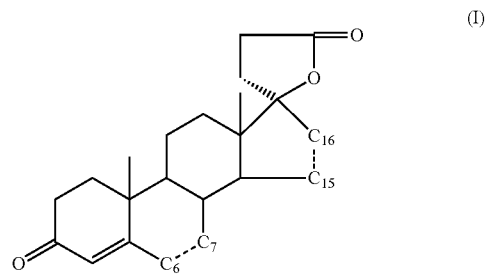

Wherein:

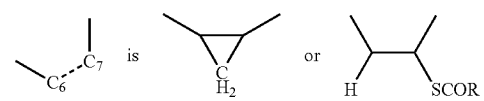

R is lower alkyl of up to 5 carbon atoms, and

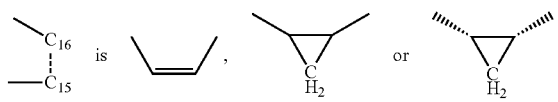

Lower alkyl residues include branched and unbranched groups, for example, methyl, ethyl and n-propyl.

Specific compounds of interest within Formula I are the following:

7α-acetylthio-3-oxo-4,15-androstadiene-[17((β-1')-spiro-5']perhydrofuran-2'-one;

3-oxo-7α-propionylthio-4,15-androstadiene-[17((β-1')-spiro-5']perhydrofuran-2'-one;

6β,7β-methylene-3-oxo4,15-androstadiene-[17((β-1')-spiro-5']perhydrofuran-2'-one;

15α,16α-methylene-3-oxo-4,7α-propionylthio-4-androstene[17(β-1')-spiro-5']perhydrofuran-2'-one;

6β,7β,15α,16α-dimethylene-3-oxo-4-androstene[17(β-1')-spiro-5']-perhydrofuran-2'-one;

7α-acetylthio-15β,16β-Methylene-3-oxo-4-androstene-[17(β-1')-spiro-5']perhydrofuran-2'-one;

15β,16β-methylene-3-oxo-7β-propionylthio-4-androstene-[17((3-1')-spiro-5']perhydrofuran-2'-one; and 6β,7β,15β,16β-dimethylene-3-oxo-4-androstene-[17(β-1')-spiro-5']perhydrofuran-2'-one.

Methods to make compounds of Formula I are described in U.S. Pat. No. 4,129,564 to Wiechart et al. issued on 12 Dec. 1978.

Another family of non-epoxy-steroidal compounds of interest is defined by Formula II:

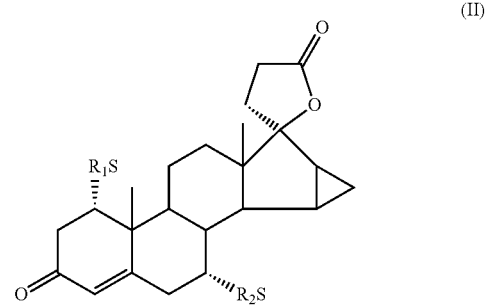

wherein R1 is C1-3-alkyl or C1-3 acyl and R2 is H or C1-3-alkyl.

Specific compounds of interest within Formula II are the following:

1α-acetylthio-15β,16β-methylene-7α-methylthio-3-oxo-17α-pregn-4-ene-21,17-carbolactone; and 15β,16β-methylene-1α,7α-dimethylthio-3-oxo-17α-pregn-4-ene-21,17-carbolactone.

Methods to make the compounds of Formula II are described in U.S. Pat. No. 4,789,668 to Nickisch et al. which issued 6 Dec. 1988.

Yet another family of non-epoxy-steroidal compounds of interest is defined by a structure of Formula III:

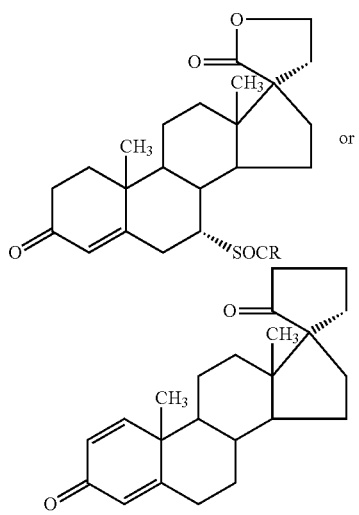

(III)

wherein R is lower alkyl, examples of which include lower alkyl groups of methyl, ethyl, propyl and butyl. Specific compounds of interest include:

3β,21-dihydroxy-17α-pregna-5,15-diene-17-carboxylic acid γ-lactone;

3β,21-dihydroxy-17α-pregna-5,15-diene-17-carboxylic acid γ-lactone 3-acetate;

3β,21-dihydroxy-17α-pregn-5-ene-17-carboxylic acid γ-lactone;

3β,21-dihydroxy-17α-pregn-5-ene-17-carboxylic acid γ-lactone 3-acetate;

21-hydroxy-3-oxo-17α-pregn-4-ene-17-carboxylic acid γ-lactone;

21-hydroxy-3-oxo-17α-pregna-4,6-diene-17-carboxylic acid γ-lactone;

21-hydroxy-3-oxo-17α-pregna-1,4-diene-17-carboxylic acid γ-lactone;

7α-acylthio-21-hydroxy-3-oxo-17α-pregn-4-ene-17-carboxylic acid γ-lactone; and

7α-acetylthio-21-hydroxy-3-oxo-17α-pregn-4-ene-17-carboxylic acid γ-lactone.

Methods to make the compounds of Formula III are described in U.S. Pat. No. 3,257,390 to Patchett which issued 21 Jun. 1966.

Still another family of non-epoxy-steroidal compounds of interest is represented by Formula IV:

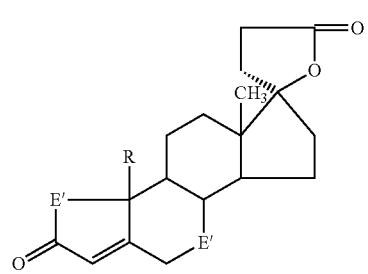

(IV)

wherein E' is selected from the group consisting of ethylene, vinylene and (lower alkanoyl) thioethylene radicals, E" is selected from the group consisting of ethylene, vinylene, (lower alkanoyl) thioethylene and (lower alkanoyl) thiopropylene radicals; R is a methyl radical except when E' and E" are ethylene and (lower alkanoyl) thioethylene radicals, respectively, in which case R is selected from the group consisting of hydrogen and methyl radicals; and the selection of E' and E" is such that at least one (lower alkanoyl) thio radical is present.

One family of non-epoxy-steroidal compounds within Formula IV is represented by Formula V:

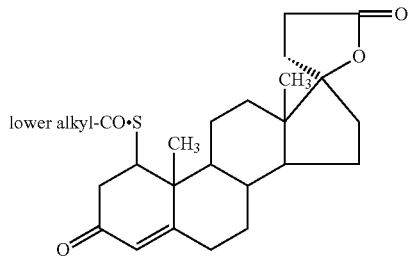

Another compound of Formula V is 1-acetylthio-17α-(2-carboxyethyl)-17β-hydroxy-androst-4-en-3-one lactone.

Another family of non-epoxy-steroidal compounds within Formula IV is represented by Formula VI:

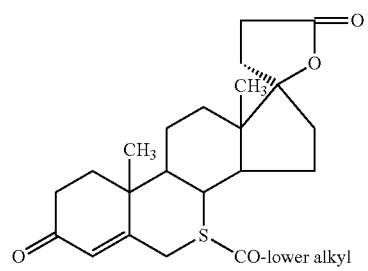

(VI)

Exemplary compounds within Formula VI include the following:

7α-acetylthio-17α-(2-carboxyethyl)-17β-hydroxy-androst-4-en-3-one lactone;

7β-acetylthio-17α-(2-carboxyethyl)-17β-hydroxy-androst-4-en-3-one lactone;

1α,7α-diacetylthio-17α-(2-carboxyethyl)-17β-hydroxy-androsta-4,6-dien-3-one lactone;

7α-acetylthio-17αe-(2-carboxyethyl)-17β-hydroxy-androsta-1,4-dien-3-one lactone;

7α-acetylthio-17α-(2-carboxyethyl)-17β-hydroxy-19-norandrost-4-en-3-one lactone; and 7α-acetylthio-17α-(2-carboxyethyl)-17β-hydroxy-6α-methylandrost-4-en-3-one lactone.

In Formulae IV-VI, the term "alkyl" is intended to embrace linear and branched alkyl radicals containing one to about eight carbons. The term "(lower alkanoyl)thio" embraces radicals of the formula lower alkyl

Of particular interest is the compound spironolactone (17-hydroxy-7α-mercapto-3-oxo-17α-pregn-4-ene-21-carboxylic acid γ-lactone acetate) having the following structure:

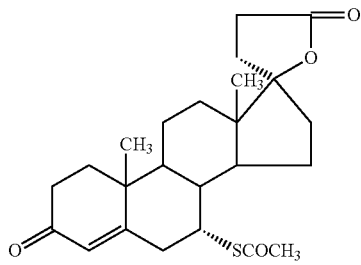

Methods to make compounds of Formulae IV-VI are described in U.S. Pat. No. 3,013,012 to Cella et al. which issued 12 Dec. 1961. Spironolactone is sold by G. D. Searle & Co., Skokie, Ill., under the trademark "ALDACTONE", in tablet dosage form at doses of 25 mg, 50 mg and 100 mg per tablet.

Another family of steroidal mineralocorticoid receptor antagonists is exemplified by drospirenone, (6R-(6α,7α,8β,9α,10β,13β,14α,15α,16α,17β))-1,3',4',6,7,8,9,10,11,12,13,14,15,16,20,21-hexadecahydro-10,13-dimethylspiro [17H-dicyclopropa(6,7:15,16)cyclopenta(a)phenanthrene-17,2' (5'H)-furan)-3,5' (2H)-dione, CAS registration number 67392-87-4. Methods to make and use drospirenone are described in patent GB 1550568 1979, priority DE 2652761 1976.

Crystalline forms that are easily handled, reproducible in form, easily prepared, stable, and which are non-hygroscopic have been identified for the mineralocorticoid receptor antagonist eplerenone. These include Form H, Form L, various crystalline solvates and amorphous eplerenone. These forms, methods to make these forms, and use of these forms in preparing compositions and medicaments, are disclosed in Barton et al., WO 01/41535 and Barton et al., WO 01/42272 both incorporated herein in their entirety.

Small organic molecules that may be used as mineralocorticoid receptor antagonists according to the invention may also be non-steroidal. For example, classes of non-steroidal MR antagonists have just begun to emerge over the past few years (Meyers, Marvin J1; Hu, Xiao Expert Opinion on Therapeutic Patents, Volume 17, Number 1, January 2007, pp. 17-23(7). Recently, dihydropyrimidines have been shown to display MR antagonism (Activation of Mineralocorticoid Receptors by Exogenous Glucocorticoids and the Development of Cardiovascular Inflammatory Responses in Adrenalectomized Rats. Young M J, Morgan J, Brolin K, Fuller P J, Funder J W. Endocrinology. 2010 Apr. 21). Furthermore, Arhancet el al. disclose other class of non-steroidal MR antagonists (Arhancet G B, Woodard S S, Dietz J D, Garland D J, Wagner G M, Iyanar K, Collins J T, Blinn J R, Numann R E, Hu X, Huang H C. Stereochemical Requirements for the Mineralocorticoid Receptor Antagonist Activity of Dihydropyridines. J Med Chem. 2010 Apr. 21). Other exemplary non-steroidal mineralocorticoid receptor antagonists include but are not limited to those described in US Patent Application Publication US 20090163472 WO2004052847, WO 2008053300 that are hereby incorporated by reference into the present disclosure. For example WO 06/076202 (published Jul. 20, 2006) reports a class of imidazole carboxamides as mineralocorticoid receptor antagonists. WO 06/012642 (published Feb. 2, 2006) reports a class of pyrrole carboxamides as mineralocorticoid receptor antagonists. WO 04/052847 (published Jun. 24, 2004) reports a class of dibenzosuberanes as mineralocorticoid receptor antagonists. WO 05/066161 (published Jul. 21, 2005) reports a class of dibenzosuberanes as mineralocorticoid receptor antagonists. WO 03/078394 (published Sep. 25, 2003) reports a class of 3,3-bisaryl oxindoles as mineralocorticoid receptor antagonists. WO 05/097118 (published Oct. 20, 2005) reports a class of 4-aryl-1,4-dihydropyridines as mineralocorticoid receptor antagonists. WO 04/067529 (published Aug. 12, 2004) reports a class of 3-benzyl indoles as mineralocorticoid receptor antagonists. WO 06/077821 (published Jul. 27, 2006) reports classes of benzoxazinethiones and tetrahydroquinolines as mineralocorticoid receptor antagonists. WO 06/010142 (published Jan. 26, 2006) reports a class of aryl benzoxazinones/thiones as mineralocorticoid receptor antagonists.

Another example of antagonist includes a salt of the canrenoic acid. Canrenoic acid is a prodrug, which is metabolized to canrenone in the body.

Alternatively, the mineralocorticoid receptor antagonist may consist in an antibody (the term including "antibody fragment"). In particular, the mineralocorticoid receptor antagonist may consist in an antibody directed against the mineralocorticoid receptor, in such a way that said antibody inhibits the receptor.

Antibodies can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies can be prepared and isolated using any technique that provides for the production of antibody molecules by continuous cell lines in culture. Techniques for production and isolation include but are not limited to the hybridoma technique; the human B-cell hybridoma technique; and the EBV-hybridoma technique. Alternatively, techniques described for the production of single chain antibodies (see, e.g., U.S. Pat. No. 4,946,778) can be adapted to produce anti-mineralocorticoid receptor single chain antibodies.

The mineralocorticoid receptor antagonist useful in practicing the present invention also include anti-mineralocorticoid receptor antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to mineralocorticoid receptor.

Humanized antibodies and antibody fragments thereof can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then after raising antibodies as above described, the skilled man in the art can easily select those that are mineralocorticoid receptor antagonist.

In another embodiment the mineralocorticoid receptor antagonist is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Then after raising aptamers directed against the mineralocorticoid receptors as above described, the skilled man in the art can easily select those that are mineralocorticoid receptor antagonists.

A further object of the invention relates to an inhibitor of mineralocorticoid receptor gene expression for use in a method for stimulating reepithelialisation of the skin or of the cornea during wound healing.

Inhibitors of expression for use in the present invention may be based on anti-sense oligonucleotide constructs. Anti-sense oligonucleotides, including anti-sense RNA molecules and anti-sense DNA molecules, would act to directly block the translation of mineralocorticoid receptor mRNA by binding thereto and thus preventing protein translation or increasing mRNA degradation, thus decreasing the level of mineralocorticoid receptor, and thus activity, in a cell. For example, antisense oligonucleotides of at least about 15 bases and complementary to unique regions of the mRNA transcript sequence encoding mineralocorticoid receptor can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566, 131; 6,365,354; 6,410,323; 6,107,091; 6,046,321; and 5,981, 732).

Small inhibitory RNAs (siRNAs) can also function as inhibitors of expression for use in the present invention. mineralocorticoid receptor gene expression can be reduced by contacting a subject or cell with a small double stranded RNA (dsRNA), or a vector or construct causing the production of a small double stranded RNA, such that mineralocorticoid receptor gene expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836). All or part of the phosphodiester bonds of the siRNAs of the invention are advantageously protected. This protection is generally implemented via the chemical route using methods that are known by art. The phosphodiester bonds can be protected, for example, by a thiol or amine functional group or by a phenyl group. The 5'- and/or 3'-ends of the siRNAs of the invention are also advantageously protected, for example, using the technique described above for protecting the phosphodiester bonds. The siRNAs sequences advantageously comprises at least twelve contiguous dinucleotides or their derivatives.

As used herein, the term "siRNA derivatives" with respect to the present nucleic acid sequences refers to a nucleic acid having a percentage of identity of at least 90% with erythropoietin or fragment thereof, preferably of at least 95%, as an example of at least 98%, and more preferably of at least 98%.

As used herein, "percentage of identity" between two nucleic acid sequences, means the percentage of identical nucleic acid, between the two sequences to be compared, obtained with the best alignment of said sequences, this percentage being purely statistical and the differences between these two sequences being randomly spread over the nucleic acid acids sequences. As used herein, "best alignment" or "optimal alignment", means the alignment for which the determined percentage of identity (see below) is the highest. Sequences comparison between two nucleic acids sequences are usually realized by comparing these sequences that have been previously align according to the best alignment; this comparison is realized on segments of comparison in order to identify and compared the local regions of similarity. The best sequences alignment to perform comparison can be realized, beside by a manual way, by using the global homology algorithm developed by SMITH and WATERMAN (Ad. App. Math., vol. 2, p:482, 1981), by using the local homology algorithm developed by NEDDLEMAN and WUNSCH (J. Mol. Biol., vol. 48, p:443, 1970), by using the method of similarities developed by PEARSON and LIPMAN (Proc. Natl. Acd. Sci. USA, vol. 85, p:2444, 1988), by using computer softwares using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C., Nucleic Acids Research, vol. 32, p:1792, 2004). To get the best local alignment, one can preferably used BLAST software. The identity percentage between two sequences of nucleic acids is determined by comparing these two sequences optimally aligned, the nucleic acids sequences being able to comprise additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

shRNAs (short hairpin RNA) can also function as inhibitors of expression for use in the present invention.

Ribozymes can also function as inhibitors of expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of mineralocorticoid receptor mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable.

Both antisense oligonucleotides and ribozymes useful as inhibitors of expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and preferably cells expressing mineralocorticoid receptor. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated (AAV) viruses, which are double-stranded DNA viruses that have already been approved for human use in gene therapy. Actually 12 different AAV serotypes (AAV1 to 12) are known, each with different tissue tropisms (Wu, Z Mol Ther 2006; 14:316-27). Recombinant AAV are derived from the dependent parvovirus AAV2 (Choi, V W J Virol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter. The promoter may be specific for Muller glial cells, microglia cells, endothelial cells, pericyte cells and astrocytes For example, a specific expression in Muller glial cells may be obtained through the promoter of the glutamine synthetase gene is suitable. The promoter can also be, e.g., a viral promoter, such as CMV promoter or any synthetic promoters.

Active ingredients of the invention (i.e. mineralocorticoid receptor antagonists and inhibitors of mineralocorticoid receptor gene expression) may be administered in the form of a pharmaceutical composition, as defined below. The active ingredients of the invention may be combined with pharmaceutically acceptable excipients, and optionally sustained-release matrices, such as biodegradable polymers, to form therapeutic compositions.

Accordingly, a further aspect of the invention relates to a pharmaceutical composition comprising an active ingredient of the invention for use in a method for stimulating reepithelialisation of the skin or of the cornea during wound healing.

The term "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention, the active ingredients of the invention can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

In a preferred embodiment, it may be desirable to administer the active ingredient of the invention in admixture with a topical pharmaceutically or cosmetically acceptable carrier. The topical pharmaceutically acceptable carrier is any substantially nontoxic carrier conventionally usable for topical administration of pharmaceuticals in which the active ingredient of the invention will remain stable and bioavailable when applied directly to skin or corneal surfaces. For example, carriers such as those known in the art effective for penetrating the keratin layer of the skin into the stratum corneum may be useful in delivering the active ingredient of the invention to the area of interest. Such carriers include liposomes. active ingredient of the invention can be dispersed or emulsified in a medium in a conventional manner to form a liquid preparation or mixed with a semi-solid (gel) or solid carrier to form a paste, powder, ointment, cream, lotion or the like.

Suitable topical pharmaceutically acceptable carriers include water, buffered saline, petroleum jelly (vaseline), petrolatum, mineral oil, vegetable oil, animal oil, organic and inorganic waxes, such as microcrystalline, paraffin and ozocerite wax, natural polymers, such as xanthanes, gelatin, cellulose, collagen, starch, or gum arabic, synthetic polymers, alcohols, polyols, and the like. The carrier can be a water miscible carrier composition. Such water miscible, topical pharmaceutically acceptable carrier composition can include those made with one or more appropriate ingredients outset of therapy.

Because dermatologic conditions to be treated may be visible, the topical carrier can also be a topical cosmetically acceptable carrier. The topical cosmetically acceptable carrier will be any substantially non-toxic carrier conventionally usable for topical administration of cosmetics in which active ingredient of the invention will remain stable and bioavailable when applied directly to the skin surface. Suitable cosmetically acceptable carriers are known to those of skill in the art and include, but are not limited to, cosmetically acceptable liquids, creams, oils, lotions, ointments, gels, or solids, such as conventional cosmetic night creams, foundation creams, suntan lotions, sunscreens, hand lotions, make-up and make-up bases, masks and the like. Topical cosmetically acceptable carriers may be similar or identical in nature to the above described topical pharmaceutically acceptable carriers. The compositions can contain other ingredients conventional in cosmetics including perfumes, estrogen, vitamins A, C or E, alpha-hydroxy or alpha-keto acids such as pyruvic, lactic or glycolic acids, lanolin, vaseline, aloe vera, methyl or propyl paraben, pigments and the like.

It may be desirable to have a delivery system that controls the release of active ingredient of the invention to the wound and adheres to or maintains itself on the wound for an extended period of time to increase the contact time of the active ingredient of the invention on the wound. Sustained or delayed release of active ingredient of the invention provides a more efficient administration resulting in less frequent and/or decreased dosage of active ingredient of the invention and better patient compliance. Examples of suitable carriers for sustained or delayed release in a moist environment include gelatin, gum arabic, xanthane polymers. Pharmaceutical carriers capable of releasing the active ingredient of the invention when exposed to any oily, fatty, waxy, or moist environment on the area being treated, include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like. Controlled delivery systems are described, for example, in U.S. Pat. No. 5,427,778 which provides gel formulations and viscous solutions for delivery of the active ingredient of the invention to a wound site. Gels have the advantages of having a high water content to keep the wound moist, the ability to absorb wound exudate, easy application and easy removal by washing. Preferably, the sustained or delayed release carrier is a gel, liposome, microsponge or microsphere.

The active ingredient of the invention can also be administered in combination with other pharmaceutically effective agents including, but not limited to, antibiotics, other wound healing agents, and antioxidants.

The route of administration of the active ingredient of the invention will depend on the site of the wound and the type and extent of the injury. Any suitable application method can be used as long as an effective amount of the active ingredient of the invention is able to reach the areas which require reepithelialisation to occur. Routes of administration include, but are not limited to, topical, transdermal and parenteral.

Typically, the ingredient of the invention will be administered by topical or transdermal application.

Topical administration for cutaneous treatment is accomplished via a topically applied solution, cream, ointment, gel or other suitable formulation healing bandage which can then be applied to the wound such that the active ingredient of the invention composition contacts the wound. Examples of suitable transdermal devices are described, for instance, in U.S. Pat. No. 4,818,540. The active ingredient of the invention can be mixed with a pharmaceutically acceptable cream, applied to the wound, and covered with an occlusive dressing. Alternatively, the wound area can be irrigated or soaked with a solution of the active ingredient of the invention. The solution will be applied two to twelve times per day. For transdermal application, the active ingredient of the invention is formulated in a composition capable of allowing the active ingredient of the invention to penetrate the skin and site of the wound. Such compositions are applied directly to the skin or incorporated into a protective carrier such as a transdermal or "patch" device. The active ingredient of the invention formulations for transdermal administration can be used to coat the fibers of an absorbent gauze dressing.

In a particular embodiment, the pharmaceutical composition of the invention for treating cornea is an ophthalmic drop or an ophthalmic ointment. The eye drop is provided in any formulation generally used, for example, in the form of an aqueous eye drop such as aqueous eye drop solution, aqueous eye drop suspension, viscous eye drop solution, solubilized eye drop solution and the like, or in the form of a non-aqueous eye drop such as a non-aqueous eye drop solution, non-aqueous eye drop suspension and the like. When the composition for treating cornea of the present invention is prepared as an aqueous eye drop, it preferably contains an additive which is usually used in an aqueous eye drop. The examples of such an additive include preservatives, isotonic agents, buffering agents, stabilizer, pH regulators or the like. When the composition is used in a form of an eye ointment, it includes any formulations usually used. For example, it can be easily produced by optionally heating an eye ointment base and mixing it with an active ingredient of the invention. The active ingredient of the invention may be optionally dissolved or suspended in a suitable solvent, for example, sterilized pure water, distilled water for injection, vegetable oil such as castor oil and the like, before mixing with the eye ointment base. The examples of the eye ointment base agent include purified lanolin, Vaseline, plastibase, liquid paraffin and the like. The above-mentioned preservative, stabilizer and the like can be optionally blended provided the object of the present invention is not hurt.

A further object of the invention relates to a method for stimulating reepithelialisation of the skin or of the cornea during curing wound healing comprising administering a subject in need thereof with a therapeutically effective amount of a mineralocorticoid receptor antagonists or an inhibitor of mineralocorticoid receptor gene expression.

By a "therapeutically effective amount" is meant a sufficient amount of the active ingredient to stimulate reepithelialisation during curing wound healing at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The invention will be further illustrated by the following examples. However, these examples should not be interpreted in any way as limiting the scope of the present invention.

EXAMPLES

Example 1

Role of MR/Aldosterone in Skin Wound Healing

We have questioned the role of the MR in skin wound healing and scar formation. Upon cutaneous injury, scar formation includes highly controlled and interdependent successive phases (inflammation, proliferation, tissue remodeling) to restore the skin defect (Lau K, Paus R, Tiede S, Day P, Bayat A: Exploring the role of stem cells in cutaneous wound healing, Exp Dermatol 2009, 18:921-933). We address the role of aldosterone/MR on the reepithelialization process, occurring in the late phase of wound healing. To this purpose, we have used a model of wound healing (Mazzalupo S, Wawersik M J, Coulombe P A: An ex vivo assay to assess the potential of skin keratinocytes for wound epithelialization, J Invest Dermatol 2002, 118:866-870) that allows to measure the contribution of the epidermis on excised skin from newborn mice. The wound healing assay consists in organotypic culture of skin explants where keratinocytes migrate off the original patch and proliferate (excentric outgrowth), mimicking the in vivo behaviour of keratinocytes at the edge of skin wounds.

We used our transgenic mouse model (K5-MR mice) with MR overexpression in basal keratinocytes (Sainte Marie Y, Toulon A, Paus R, Maubec E, Cherfa A, Grossin M, Descamps V, Clemessy M, Gasc J M, Peuchmaur M, Glick A, Farman N, Jaisser F: Targeted skin overexpression of the mineralocorticoid receptor in mice causes epidermal atrophy, premature skin barrier formation, eye abnormalities, and alopecia, Am J Pathol 2007, 171:846-860) to question the impact of MR in neonatal skin wound healing. Briefly, skin was excised from newborn double-transgenic mice and their control littermates (less than 1 day old, i.e. at a stage preceeding the early post-natal death of K5-MR pups). Pieces of skin were cut and 4 mm sterile punchs were placed in wells of a 24-well-tissue culture plate. Thereafter, 250 microliters of medium were added, and the explants were cultured for 7 days as described in Mazzalupo et al (see supra). Explant medium was DMEM-Ham F12 (2/1), added with, 1 ml penicillin-streptomycin, 1 ml non essential amino acids, 1 ml L-glutamine, adenine $2.10^{-4}$M, insulin 5 µg/ml, T3 $2.10^{-9}$M, transferrin 5 ug/ml, cholera toxin $10^{-10}$M, hydrocortisone $10^{-6}$M, fungizone 0.5 µg/mL, decomplected fetal bovine serum 10%, epidermal growth factor 10 ng/ml, for 100 ml medium. After one week culture, skin explants were fixed in 4% paraformaldehyde (10 min) followed by methanol (5 min), and samples were processed for keratin 17 (K17) or K6 immunohistochemistry to visualize the area of keratinocyte outgrowth. The surface area of keratinocyte outgrowth was quantified (Image J NIH software).

The main finding of this study is the strikingly reduced keratinocyte outgrowth in the skin patches from K5-MR pups, compared to control animals. While explants for normal pups are surrounded by growing keratinocytes forming a homogenous area of outgrowth stained with the anti-keratin antibody, we observed that keratinocytes issued from K5-MR pups formed a much smaller outgrowth with irregular edges. Quantification of the surface of outgrowth revealed a major difference between control and K5-MR skin behaviour. Indeed the area of keratinocyte outgrowth was $30.6 \pm 1.31$ mm$^2$ in CT versus $17.7 \pm 1.22$ mm$^2$ in K5-MR (mean and SEM, $p<0.0001$, n=28 and 30 pups respectively, issued from 10 different litters). Thus MR overexpression in basal keratinocytes reduces their epithelialization behaviour. To establish the link between the altered outgrowth observed in skin explants of K5-MR mice and MR overexpression, this assay was repeated in the presence of the MR antagonist potassium canrenoate, added to the culture medium. When the skin punches were incubated with potassium canrenoate (0.1 mM), the impaired keratinocyte outgrowth of the explants from K5-MR pups was partially but significantly improved, while the antagonist had no effect in explants from control pups. Therefore, it can be concluded that MR overexpression limits the epithelial component of wound healing, in this ex vivo assay on mouse skin. Mineralocorticoid receptor antagonists should therefore stimulate reepithelialisation of the skin or of the cornea during wound healing Example 2

The Epithelial Sodium Channel ENaC as a Target of MR in Skin Wound Healing

Aldosterone/MR activation regulates genes involved in sodium transport in classical mineralocorticoid target tissues such as the renal collecting duct (Farman N, Rafestin-Oblin ME: Multiple aspects of mineralocorticoid selectivity, Am J Physiol Renal Physiol 2001, 280:F181-192; Viengchareun S, Le Menuet D, Martinerie L, Munier M, Pascual-Le Tallec L, Lombes M: The mineralocorticoid receptor: insights into its molecular and (patho) physiological biology, Nucl Recept Signal 2007, 5:e012). Renal MR activation triggers transcription (or repression) of several genes that ultimately result in an increase in the activity and number of sodium transporters or channels. In a typical epithelial target cell for aldosterone, such as the renal collecting duct principal cell, the sodium entry into the cell depends on the amiloride-sensitive apical sodium channels (ENaC, for Epithelium Sodium Channel) that are the limiting step for transepithelial sodium transport (Rossier B C, Pradervand S, Schild L, Hummler E: Epithelial sodium channel and the control of sodium balance: interaction between genetic and environmental factors, Annu Rev Physiol 2002, 64:877-897). ENaC is formed of 3 subunits (alpha, beta and gamma) that form the sodium pore. Physiological mechanisms regulating channel subunits trafficking to the membrane (with important role of the serum and glucocorticoid Induced kinase sgk1), activation by serine-proteases (as Channel Activating Proteases Cap1 and Cap3) as well as retrieval from the apical membrane are of major importance to control sodium reabsorption (Rossier B C, Stutts M J: Activation of the Epithelial Sodium Channel (ENaC) by Serine Proteases, Annu Rev Physiol 2008; Rotin D, Schild L: ENaC and its regulatory proteins as drug targets for blood pressure control, Curr Drug Targets 2008, 9:709-716).

We have shown that the sodium channel ENaC is also expressed by keratinocytes (Brouard M, Casado M, Djelidi S, Barrandon Y, Farman N: Epithelial sodium channel in human epidermal keratinocytes: expression of its subunits and relation to sodium transport and differentiation, J Cell Sci 1999, 112 (Pt 19):3343-3352; Roudier-Pujol C, Rochat A, Escoubet B, Eugene E, Barrandon Y, Bonvalet J P, Farman N: Differential expression of epithelial sodium channel subunit mRNAs in rat skin, J Cell Sci 1996, 109 (Pt 2):379-385) furthermore the knock out of its alpha-subunit in the epidermis results in epidermal hyperplasia (Mauro T, Guitard M, Behne M, Oda Y, Crumrine D, Komuves L, Rassner U, Elias P M, Hummler E: The ENaC channel is required for normal epidermal differentiation, J Invest Dermatol 2002, 118:589-594). Enhanced beta ENaC expression has been reported during differentiation of cultured human keratinocytes (Brouard M, Casado M, Djelidi S, Barrandon Y, Farman N: Epithelial sodium channel in human epidermal keratinocytes: expression of its subunits and relation to sodium transport and differentiation, J Cell Sci 1999, 112 (Pt 19):3343-3352). It was also observed that ENaC inhibitors impaired the formation of domes in confluent keratinocyte monolayers (Brouard M, Casado M, Djelidi S, Barrandon Y, Farman N: Epithelial sodium channel in human epidermal keratinocytes: expression of its subunits and relation to sodium transport and differentiation, J Cell Sci 1999, 112 (Pt 19):3343-3352). Altogether, these data suggest that ENaC may play a role in the epidermis that remains to be fully elucidated. The epidermis also expresses high levels of some serine proteases belonging to signalling cascades that modify ENaC activity in aldosterone-sensitive epitheliums. Matriptase (also named MT/SP1 or Cap 3) cleaves the inactive form of prostasin (Cap1 or PRSS8) into an active protease that activates ENaC. Interestingly, knock out of the ENaC-activating serine-protease Cap1 leads to severe impairment of skin barrier permeability; Cap3 knock out also results in impaired epidermal barrier function. However there is no information on the possible involvement of ENaC in wound healing.

We took advantage of the K5-MR mouse model to question whether expression of ENaC and its main regulators may be altered by MR overexpression. Skin samples from control and K5-MR neonates were processed for real-time PCR analysis of gene expression. We show that MR overexpression in the epidermis leads to enhanced skin mRNA expression of all 3 subunits of ENaC, while sgk1, Cap1 and Cap3 levels were comparable to those of control mice. This abnormal pattern of expression is blunted when pregnant mice were given canrenoate, indicating that the increase in ENaC expression in the epidermis of K5-MR pups is indeed due to MR activity.

Example 3

Role of MR/Aldosterone in Corneal Wound Healing

As the epidermis, the epithelium of the cornea is a multi-stratified malphigian epithelium; it is formed of several layers of cells, with basal proliferative cells that progressively migrate towards the surface, when they enter into the terminal differentiation program. We have recently identified the mineralocorticoid receptor in the mouse and rat corneal epithelium, located by immunohistochemistry to the basal layers of the epithelium. We also have preliminary data that indicate that aldosterone regulates the expression of ion/water channel in the rat cornea. By analogy to the skin, it can be anticipated that the corneal MR may be involved in the epithelial wound healing of the cornea.

REFERENCES

Throughout this application, various references describe the state of the art to which this invention pertains. The disclosures of these references are hereby incorporated by reference into the present disclosure.

The invention claimed is:

1. A method for stimulating reepithelialization of skin of a subject in need thereof, comprising the steps of:
locating a wound on a dermal surface of said subject;
providing to keratinocytes at said wound of said subject a therapeutically effective amount of a mineralocorticoid receptor (MR) antagonist wherein said MR antagonist is selected from the group consisting of epoxy-steroidal mineralocorticoid receptor antagonist compounds and non-steroidal receptor antagonist compounds, wherein said step of providing is carried out during a phase of new tissue formation that includes reepithelialization; and
stimulating reepithelialization of said skin of said subject at said wound site during said phase of new tissue formation.

2. The method of claim 1, wherein said MR antagonist is selected from the group consisting of drospirenone and eplerenone.

3. The method of claim 1, wherein said step of providing is carried out by topical delivery or transdermal delivery.

4. The method of claim 3, wherein said topical delivery is cutaneous.

5. The method of claim 1 wherein said wound is selected from the group consisting of a diabetic foot ulcer, a venous stasis ulcer, and a burn.

6. The method of claim 1 wherein said wound is a site of delayed wound healing selected from the group consisting of an aging defect, a surgical scar, a finger crack after cold exposure, a nail pathology, and a foot blister.

7. The method of claim 1, wherein said epoxy-steroidal mineralocorticoid receptor antagonist compound is selected from the group consisting of Pregn-4-ene-7,21-dicarboxylic acid, 9,11-epoxy-17-hydroxy-3-oxo-, dimethyl ester, (7α, 11α,17β), 3' H-cyclopropa[6,7]pregna-4,6-diene-21-carboxylic acid, 9,11-epoxy-6,7-dihydro-17-hydroxy-3-oxo-, γ-lactone, (6β,7β,11α,17β), Pregn-4-ene-7,21-dicarboxylic acid, 9,11-epoxy-17-hydroxy-3-oxo-, 7-(1-methylethyl) ester, monopotassium salt, (7α,11α,17β), Pregn-4-ene-7,21-dicarboxylic acid, 9,11-epoxy-17-hydroxy-3-oxo-, 7-methylethyl) ester, monopotassium salt, (7α,11α,17β), 3' H-cyclopropa[6,7]pregna-1,4,6-triene-21-carboxylic acid, 9,11-epoxy-6,7-dihydro-17-hydroxy-3-oxo-, γ-lactone(6β,7β,11α), 3' H-cyclopropa[6,7]pregna-4,6-diene-21-carboxylic acid, 9,11-epoxy-6,7-dihydro-17-hydroxy-3-oxo-, methyl ester, (6β,7β,11α,17β), 3' H-cyclopropa[6,7]pregna-4,6-diene-21-carboxylic acid, 9,11-epoxy-6,7-dihydro-17-hydroxy-3-oxo-, monopotassium salt, (6β,7β,11α,17β), 3' H-cyclopropa[6,7]pregna-1,4,6-triene-21-carboxylic acid, 9,11-epoxy-6,7-dihydro-17-hydroxy-3-oxo-, γ-lactone(6β, 7β,11α,17β), Pregn-4-ene-7,21-dicarboxylic acid, 9,11-epoxy-17-hydroxy-3-oxo-, γ-lactone, ethyl ester, (7α,11α, 17β), and Pregn-4-ene-7,21-dicarboxylic acid, 9,11-epoxy-17-hydroxy-3-oxo-, γ-lactone, 1-methylethyl ester (7α,11α, 17β).

8. The method of claim 1, wherein said non-steroidal receptor antagonist compound is selected from the group consisting of Dihydropyridines, imidazole carboxamides, pyrrole carboxamides, dibenzosuberanes, 3,3-bisaryl oxindoles, 4-aryl-1,4-dihydropyridines, 3-benzyl indoles, benzoxazinethiones, tetrahydroquinolines, aryl benzoxazinones/thiones, and aryl benzoxazinethiones.

9. A method for stimulating reepithelialization of a cornea of a subject in need thereof, comprising the steps of:
locating a wound on said cornea of said subject;
providing to epithelium at said cornea of said subject a therapeutically effective amount consisting of a mineralocorticoid receptor (MR) antagonist wherein said MR antagonist is selected from the group consisting of epoxy-steroidal mineralocorticoid receptor antagonist compounds and non-steroidal receptor antagonist compounds, wherein said step of providing is carried out during a phase of new tissue formation that includes reepithelialization; and
stimulating reepithelialization of said corneal epithelium of said subject at said wound site during said phase of new tissue formation.

10. The method of claim 9 wherein said wound is selected from the group consisting of a corneal ulcer, a site of corneal erosion or trauma, and a site of a keratoplasty.

11. The method of claim 9 wherein said wound is dry eye.

12. The method of claim 9, wherein said MR antagonist is selected from the group consisting of drospirenone and eplerenone.

13. The method of claim 9, wherein said step of providing is carried out by topical delivery or transdermal delivery.

14. The method of claim 13, wherein said topical delivery is ophthalmic.

15. The method of claim 9, wherein said epoxy-steroidal mineralocorticoid receptor antagonist compound is selected from the group consisting of Pregn-4-ene-7,21-dicarboxylic acid, 9,11-epoxy-17-hydroxy-3-oxo-, dimethyl ester, (7α, 11α,17β), 3' H-cyclopropa[6,7]pregna-4,6-diene-21-carboxylic acid, 9,11-epoxy-6,7-dihydro-17-hydroxy-3-oxo-, γ-lactone, (6β,7β,11α,17β), Pregn-4-ene-7,21-dicarboxylic acid, 9,11-epoxy-17-hydroxy-3-oxo-, 7-(1-methylethyl) ester, monopotassium salt, (7α,11α,17β), Pregn-4-ene-7,21-dicarboxylic acid, 9,11-epoxy-17-hydroxy-3-oxo-, 7-methylethyl) ester, monopotassium salt, (7α,11α,17β), 3' H-cyclopropa[6,7]pregna-1,4,6-triene-21-carboxylic acid, 9,11-epoxy-6,7-dihydro-17-hydroxy-3-oxo-, γ-lactone(6β,7β, 11α), 3' H-cyclopropa[6,7]pregna-4,6-diene-21-carboxylic acid, 9,11-epoxy-6,7-dihydro-17-hydroxy-3-oxo-, methyl ester, (6β,7β, 11α,17β), 3' H-cyclopropa[6,7]pregna-4,6-diene-21-carboxylic acid, 9,11-epoxy-6,7-dihydro-17-hydroxy-3-oxo-, monopotassium salt, (6β,7β,11α,17β), 3' H-cyclopropa[6,7]pregna-1,4,6-triene-21-carboxylic acid, 9,11-epoxy-6,7-dihydro-17-hydroxy-3-oxo-, γ-lactone(6β, 7β,11α,17β), Pregn-4-ene-7,21-dicarboxylic acid, 9,11-epoxy-17-hydroxy-3-oxo-, γ-lactone, ethyl ester, (7α,11α, 17β), and Pregn-4-ene-7,21-dicarboxylic acid, 9,11-epoxy-17-hydroxy-3-oxo-, γ-lactone, 1-methylethyl ester (7α,11α, 17β).

16. The method of claim 9, wherein said non-steroidal receptor antagonist compound is selected from the group consisting of Dihydropyridines, imidazole carboxamides, pyrrole carboxamides, dibenzosuberanes, 3,3-bisaryl oxindoles, 4-aryl-1,4-dihydropyridines, 3-benzyl indoles, benzoxazinethiones, tetrahydroquinolines, aryl benzoxazinones/thiones, and aryl benzoxazinethiones.

* * * * *